(12) United States Patent
Swalwell

(10) Patent No.: US 8,467,054 B2
(45) Date of Patent: Jun. 18, 2013

(54) VIRTUAL CORE FLOW CYTOMETRY

(75) Inventor: Jarred E. Swalwell, Shoreline, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 13/145,772

(22) PCT Filed: Jan. 22, 2010

(86) PCT No.: PCT/US2010/021787
§ 371 (c)(1),
(2), (4) Date: Oct. 3, 2011

(87) PCT Pub. No.: WO2010/085632
PCT Pub. Date: Jul. 29, 2010

(65) Prior Publication Data
US 2012/0050738 A1 Mar. 1, 2012

Related U.S. Application Data

(60) Provisional application No. 61/147,035, filed on Jan. 23, 2009, provisional application No. 61/147,060, filed on Jan. 23, 2009.

(51) Int. Cl.
*G01N 21/00* (2006.01)
(52) U.S. Cl.
USPC ............................... 356/343; 356/337
(58) Field of Classification Search
USPC ............ 356/600–624, 121–127, 337–343, 356/39, 441–442; 359/346, 721, 744, 642; 382/133; 250/461.2, 573–574, 564–565; 422/73; 436/63
See application file for complete search history.

(56) References Cited

U.S. PATENT DOCUMENTS

| | | | |
|---|---|---|---|
| 2,037,014 A | 4/1936 | Eitzen |
| 2,072,478 A | 3/1937 | Gray |
| 3,482,107 A | 12/1969 | Hock |
| 4,732,479 A | 3/1988 | Tanaka |
| 4,813,031 A | 3/1989 | Bierhoff |
| 5,133,602 A | 7/1992 | Batchelder |

(Continued)

OTHER PUBLICATIONS

Preliminary Report on Patentability mailed Jul. 26, 2011, in corresponding International Application No. PCT/US2010/021787, filed Jan. 22, 2010, 5 pages.

(Continued)

*Primary Examiner* — Tri T Ton
(74) *Attorney, Agent, or Firm* — Christensen O'Connor Johnson Kindness PLLC

(57) ABSTRACT

A sheathless flow cytometry system is disclosed wherein a fluid containing particles of interest, for example cells, flows through a sensing region, and is illuminated in the sensing region with one or more light source. Light resulting from the interaction of the particles with the illumination is received by an objective, and focused toward a field stop having an aperture comprising relatively large end portions and a relatively small center portion. Light deflectors, such as prisms, are disposed over the relatively large end portions of the aperture. The system is arranged such that light from particles in focus in the sensing region is focused on the relatively small center portion of the aperture. Peripheral detectors are positioned to receive light from the light deflectors, and a scatter detector is positioned to receive light passing through the center portion. The detector signals may be used to identify which of the detector signals correspond to particles in focus as they passed through the sensing region.

18 Claims, 9 Drawing Sheets

U.S. PATENT DOCUMENTS

| | | |
|---|---|---|
| 5,350,695 A | 9/1994 | Colella |
| 5,353,073 A | 10/1994 | Kobayashi |
| 5,739,902 A | 4/1998 | Gjelsnes |
| 5,760,900 A | 6/1998 | Ito |
| 5,844,685 A | 12/1998 | Gontin |
| 6,697,163 B2 | 2/2004 | Fukuda |
| 6,982,785 B2 | 1/2006 | van den Engh |
| 7,315,357 B2 | 1/2008 | Ortyn |
| 7,410,809 B2 | 8/2008 | Goix |
| 7,728,974 B2 | 6/2010 | van den Engh |
| 2008/0186479 A1 | 8/2008 | Swalwell |

OTHER PUBLICATIONS

International Search Report mailed Oct. 11, 2010, issued in corresponding International Application No. PCT/US2010/021787, filed Jan. 22, 2010, 5 pages.

VIRTUAL CORE FLOW CYTOMETRY

CROSS-REFERENCES TO RELATED APPLICATIONS

This application claims the benefit of U.S. Provisional Application No. 61/147,060, filed Jan. 23, 2009, and further claims the benefit of U.S. Provisional Application No. 61/147,035, filed Jan. 23, 2009, the disclosures of which are hereby expressly incorporated by reference in their entirety.

STATEMENT OF GOVERNMENT LICENSE RIGHTS

This invention was made with Government support under Contract No. OCE 622247 awarded by the National Science Foundation. The Government has certain rights in the invention.

BACKGROUND

With conventional flow cytometers, particles, such as cells, are aligned and carried along ideally in a single file arrangement within a stream of clear fluid, also known as a sheath fluid, to pass before one or more beams of light in an sensing region (or the detection optics) for subsequent detection of various parametric characteristics to classify, categorize, quantify or otherwise detect one or more aspects of the particles. This sheath fluid guides the particles substantially along a desired path such that the particles are at an in-focus position in the sensing region relative to one or more beams of light for subsequent sensing by detectors and automated quantification of cells according to predetermined parametric characteristics. Without the sheath fluid, particles while in the sensing region may not be in a proper in-focus position relative to the beams of light directed into the sensing region so that detection data would be collected regarding out-of-focus and in-focus particles. The detection data collected regarding the out-of-focus particles would lack accuracy and consequently harm the overall integrity of the data collected.

Due to the single-file nature of the particles passing in the sheath fluid, for each particle passing through or in the vicinity of one or more of the light beams in an sensing region, there is generally little or no surrounding particles so that there is little background light scatter or fluorescence to interfere with detection of the predetermined one or more parametric characteristics associated with the particle so that each of the particles can be considered as in-focus while in the sensing region with respect to the one or more beams of light involved. Unfortunately, the need for both clean sheath fluid and a highly stable stream greatly complicates the fluidics of these systems. As a consequence, setup and maintenance of these systems while measurements are being performed is very labor intensive. In addition, related system design such as involving sheath fluid management and sample injection constitute a significant proportion of the complexity found with conventional flow cytometry systems.

SUMMARY

A sheathless cytometry system and method are disclosed wherein a sheathless fluid stream with a plurality of suspended particles is illuminated at a sensing region with a light source, for example one or more lasers. An objective is positioned to receive light from the sensing region. The received light may include forward scatter, back scatter or side scatter light (depending on the geometry of the system) from the particles in the stream, and may include fluorescence light from the particles. A lens focuses the light from the objective onto a field stop having a shaped optical aperture. The shaped aperture includes two relatively large end portions and a relatively small center portion. When the system is properly aligned, the light from a virtual core of the fluid stream is focused on the relatively small center portion. A light detector system including an FSC detector and first and second peripheral light detectors are positioned to receive light passing through the shaped aperture. A first light deflector is positioned over the relatively large first end portion of the shaped aperture and operable to deflect light towards the first peripheral light detector, and a second light deflector is positioned over the relatively large second end portion of the shaped aperture and operable to deflect light towards the second peripheral light detector. A controller receives signals from the FSC detector and from peripheral light detectors. The system allows the selection of data from the FSC detector that corresponds to particles that pass through the virtual core of the fluid stream.

In an embodiment of the system and method the shaped aperture is H-shaped, the light deflectors are prisms, and the light detectors are photomultiplier tubes. In another embodiment the shaped aperture is defined by a large optical aperture stop having a pair of light blocking elements disposed radially from opposite sides of the large aperture.

In an embodiment of the system the controller selects signals from the scatter light detector for use in further analysis based on the corresponding signals received from the first and second peripheral light detectors, for example the forward scatter light detector signals received by the controller are disregarded if the ratio of the corresponding signal from at least one of the first and second peripheral light detectors to the forward scatter light detector signal exceeds a predetermined value.

In an embodiment of the method of cytometry a sheathless fluid stream containing a plurality of the microscopic particles flows through a sensing region, and a light source illuminates the sensing region such that at least some of the microscopic particles in the fluid stream scatter the transmitted light. A field stop having a shaped optical aperture in alignment with the transmitted light is provided, wherein the shaped aperture includes a relatively small center portion and relatively large first and second end portions. Light deflectors are disposed over the relatively large end portions of the shaped aperture. Light scattered by the microscopic particles in the core of the stream is focused on the center portion of the shaped aperture. A scatter light detector detects light passing through the center portion of the shaped aperture to produce a scatter light signal, and peripheral light detectors detect light deflected by the light deflectors to produce deflected light signals. The deflected light signals are used to identify scatter light signals that correspond to microscopic particles passing through the focal core of the stream.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
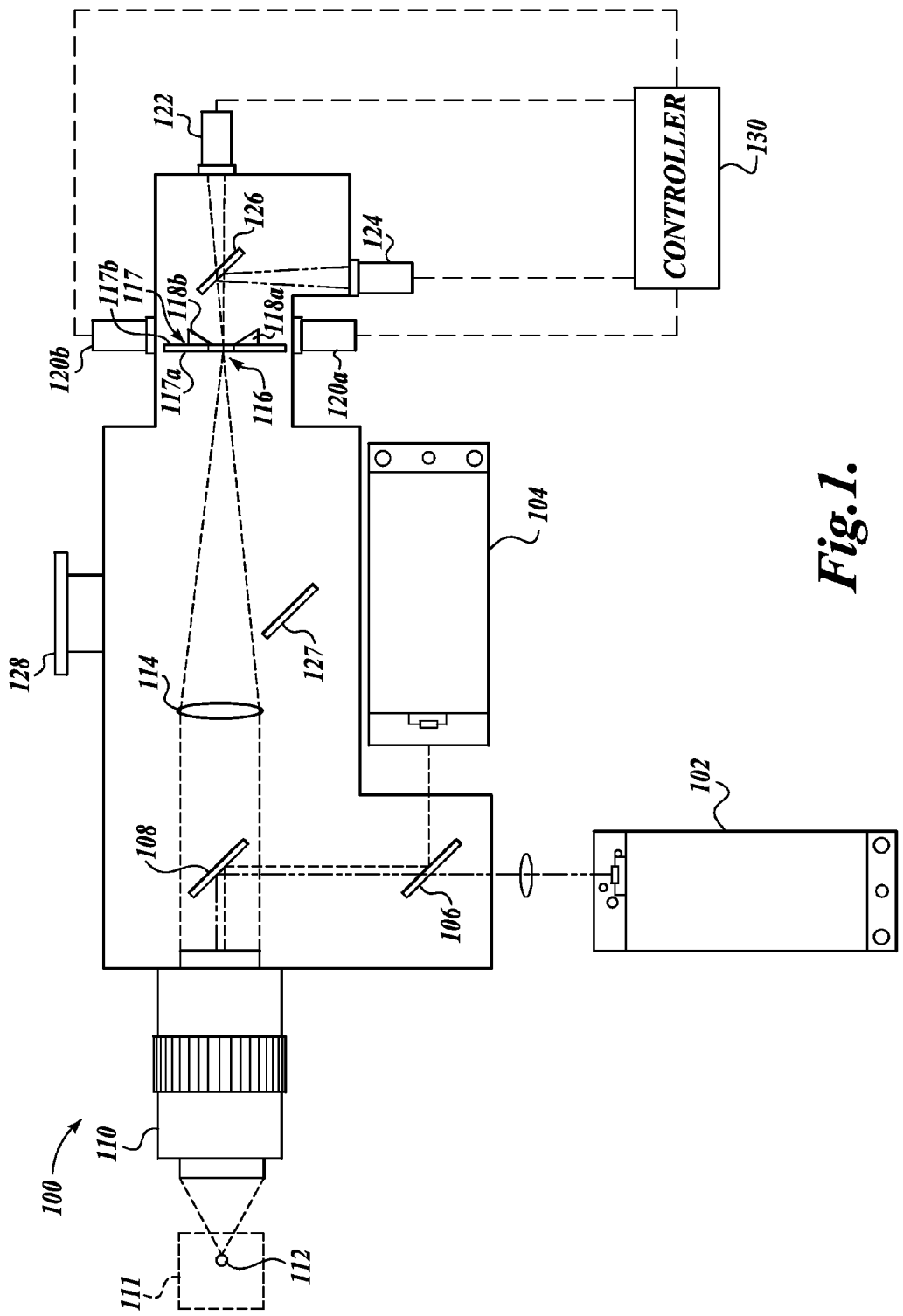
FIG. 1 is a schematic diagram of an cytometry system in accordance with the present invention.

A cytometry system and method is disclosed that reduces or eliminates the need for a sheath fluid in flow cytometry. A related Enhanced Detection System and Method is disclosed in U.S. Patent Pub. No. 2008/0186479, which is hereby incorporated by reference in its entirety. In conventional cytometers a thin stream of sample fluid is entrained in the center of a clear sheath fluid to precisely position the thin stream (and particles such as cells disposed in the thin stream) to pass through a focused laser beam. The accuracy and repeatability of the resulting measurements are dependent on the stability of the sheath/sample tandem and on the cleanliness of the sheath fluid. Unfortunately, the availability and purity of the sheath fluid constrains the use of conventional flow cytometers to well-controlled, hygienic environments.

The cytometry method and system disclosed herein avoids the need for a sheath fluid. A sample fluid forms a fluid stream through a sensing region without a sheath fluid. A light source, typically a laser, is focused on the sensing region within the fluid cell. Other types of light sources may alternatively be used. Only a portion of the particles of interest in the sample fluid will pass through the focus. Particles detected by the cytometer that do not pass through the focal portion of the sensing region will be out of focus or improperly positioned for the detectors. The system and method disclosed herein identifies which of the detected particles were not in focus in the sensing region of the fluid stream. In the disclosed systems the detection signals from out-of-focus particles are discarded. Only data detected for particles that in focus are used in the analysis to detect parametric characteristics thereof.

In some implementations, particle position signals generated through electronic circuitry are input to software- or hardware-based filtering to disregard detection of one or more predetermined parametric characteristics for particles that are not at a predetermined in-focus position while in the sensing region. In some implementations, the presence of a properly positioned particle, such as an in-focus particle, can be ascertained with a sensing system based upon confocal microscopy. Other implementations can use other ways to determine which particles in a flow of particles occupy a predetermined position, such as an in-focus position, while in a sensing region. Confocal microscopy teaches that images related to properly positioned particles, such as in-focus particles, will be focused to pass through an optical aperture, such as a pinhole mirror, which can then be received by a single selectively positioned detector, while images related to improperly positioned particles, such as out-of-focus particles, will be unfocused thereby casting light in a plurality of directions that can then be detected by appropriately placed detectors. Signals sent from the detectors can then be analyzed to ascertain status regarding whether each particle in a flow of particles is positioned while in a sensing region either in an in-focus position or an out-of-focus position.

Implementations of the enhanced detection system can be operated without using a sheath fluid and thus can be used to directly analyze environmental samples such as ocean, lake, and stream water. The enhanced detection system provides an added convenience with compactness, few moving parts, relatively low power requirements, and ease of operation that can be exploited in many applications, such as found with use in remote locations and unattended operation. Another aspect of the enhanced detection system is that the technique may be extended to incorporate other cytometric measurements involving additional lasers, scattering, apertures, fluorescence bands, and/or polarization measurements.

An exemplary cytometry system 100 in accordance with the present invention is shown schematically in FIG. 1. A first laser 102 having a first wavelength (e.g. 532 nm) and a second laser 104 having a second wavelength (e.g., 638 nm) are focused on a sensing region 111 within the fluid stream. (Note that in FIG. 1 the fluid stream direction of flow is generally perpendicular to the plane of the drawing.) The cytometry system 100 includes a dichroic mirror 106 (selectively passes light of the first wavelength and reflects light of the second wavelength), a prism 108 (or mirror or other reflector) and a microscope objective 110 (this embodiment uses confocal illumination) to illuminate a sensing region 111 shown as containing an in-focus particle 112.

A lens 114 is positioned to receive light from the objective 110, and to focus light from interactions with particles in the sensing region 111. The focus light is directed toward a field stop 117 having an optical aperture 116 to image the sensing region 111 under a limited field of view. The field stop 117 has a proximal side 117a and a distal side 117b. Located adjacent portions of the aperture 116 on the distal side 117b of the field stop 117 are a first peripheral prism 118a (or other such diverter) and a second peripheral prism 118b.

A first peripheral detector 120a and a second peripheral detector 120b are located to receive light transmitted through the first peripheral prism 118a and the second peripheral prism 118b, respectively. In a current embodiment the detectors discussed herein comprise photomultiplier tubes (PMT), although it will be readily apparent that other types of light detectors may alternatively be used, as are known in the art. The system 100 further includes a first parametric characteristics detector 122 and a second parametric characteristics detector 124 each receiving light of different wavelengths according to a second dichroic mirror 126. In aggregate, these components provide cytometric information about cells or other particles passing through the sensing region 111 by measuring the scattered light and fluorescence, for example detecting light at two (or more) different excitation wavelengths. By adding more apertures, the functionality of the sensor can be extended by adding a number of laser lines to excite other fluorophores, for example.

When a particle in the sensing region 111 is in-focus, light from the interaction of the in-focus particle with the first and second lasers 102, 104 (e.g., scatter and/or fluorescence) will be focused by the lens 114 generally through the center of the aperture 116 so that the first parametric characteristics detector 122 and the second parametric characteristics detector 124 will sense the light as shown in FIG. 1. FIG. 1 illustrates a back-scatter measuring cytometer, although other geometries are possible, and contemplated by the present invention.

The enhanced detection system 100 optionally includes a CCD camera 128 and an associated mirror 127, that is positioned to image the proximal side 117a of the field stop 117. In the current embodiment the proximal side 117a is also mirrored, whereby the CCD camera 128 can image through the sensing region 111 and laser illumination for such things as alignment. Additionally, the CCD camera 128 gives the option of imaging larger particles.

Figure 2:
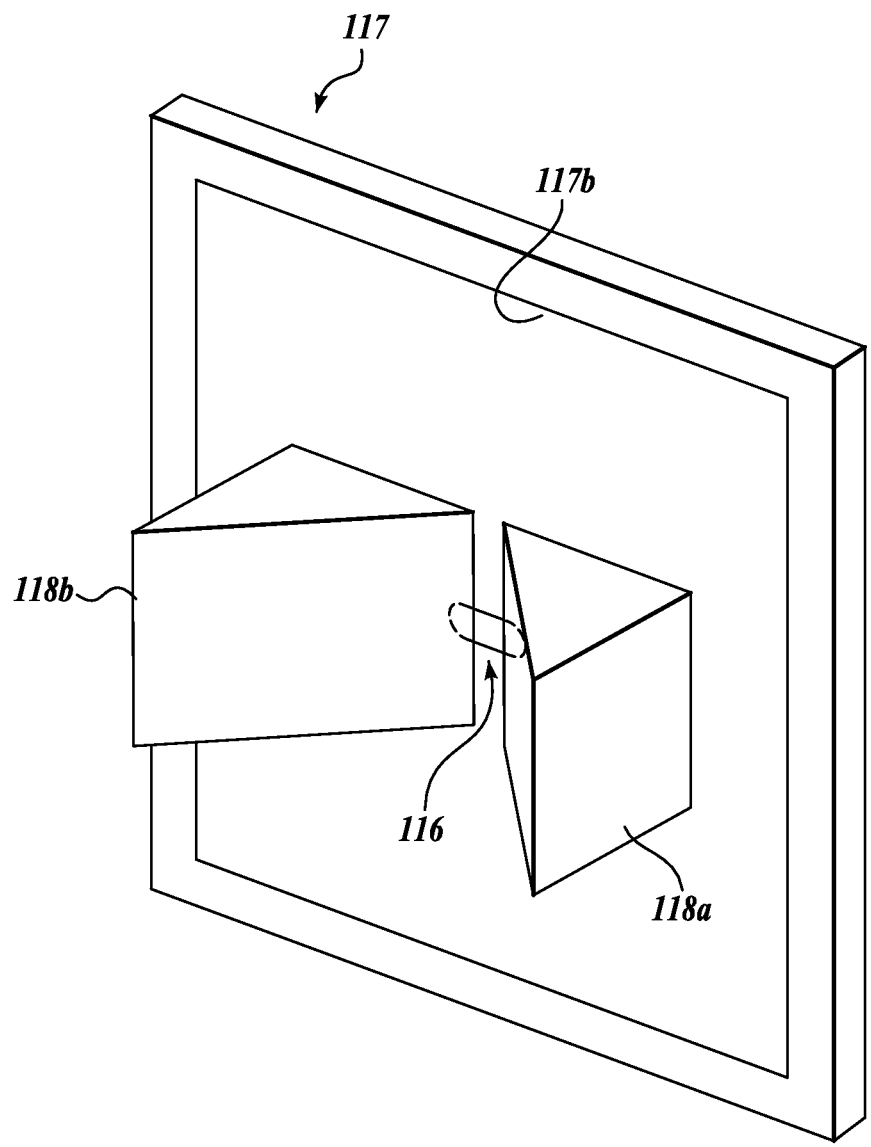
FIG. 2 is a perspective view of a portion of the field stop for the cytometry system shown in FIG. 1.

The aperture 116, the field stop 117 (distal side 117b), the first peripheral prism 118a, and the second peripheral prism 118b are shown in FIG. 2 in an enlarged view. It can now be seen that the aperture 116 comprises an elongated optical aperture 116 wherein the first peripheral prism 118a and the second peripheral prism 118b overly end portions of the elongate aperture 116.

As discussed above, interaction light from a particle positioned in the in-focus region of the sensing region 111 is focused on the center of the aperture 116, and will generally continue toward the first parametric characteristics detector 122 and the second parametric characteristics detector 124. Light from particles that are out-of-focus, i.e., out of the focal area, will not be focused on the center of the aperture 116, and will generally be at least partially redirected by the first and/or second peripheral prisms 118a, 118b. The redirected light is thereby directed toward the first peripheral detector 120a and the second peripheral detector 120b, respectively.

As indicated by dashed lines in FIG. 1, the detectors 120a, 120b, 122 and 124 are operatively connected to a controller 130. Signals generated by the first and second peripheral detectors 120a, 120b can be used by the controller 130 to gate out measurements (signals) from the first and second parametric characteristics detectors 122, 124. For example, parametric detector signals related to particles that were out-of-focus while in the sensing region 111 may be ignored, such that only signals for particles detected passing through the focal portion (or virtual core) of the fluid stream are included for further analysis.

Figure 3B:
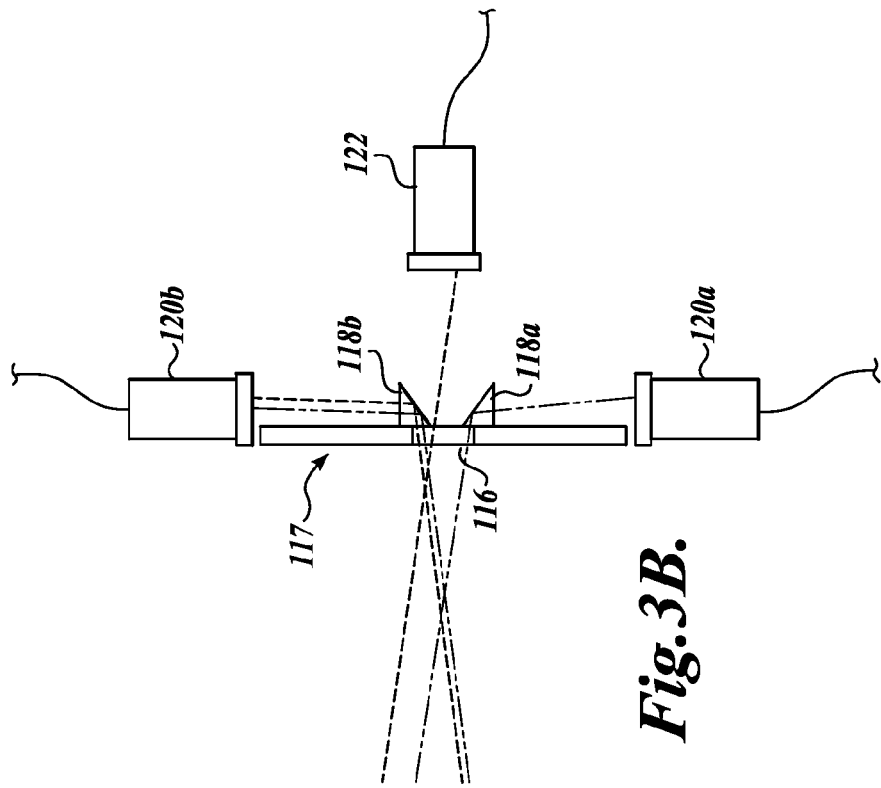
FIG. 3B is a similar schematic view as FIG. 3A, for out-of-focus particles.
Figure 3A:
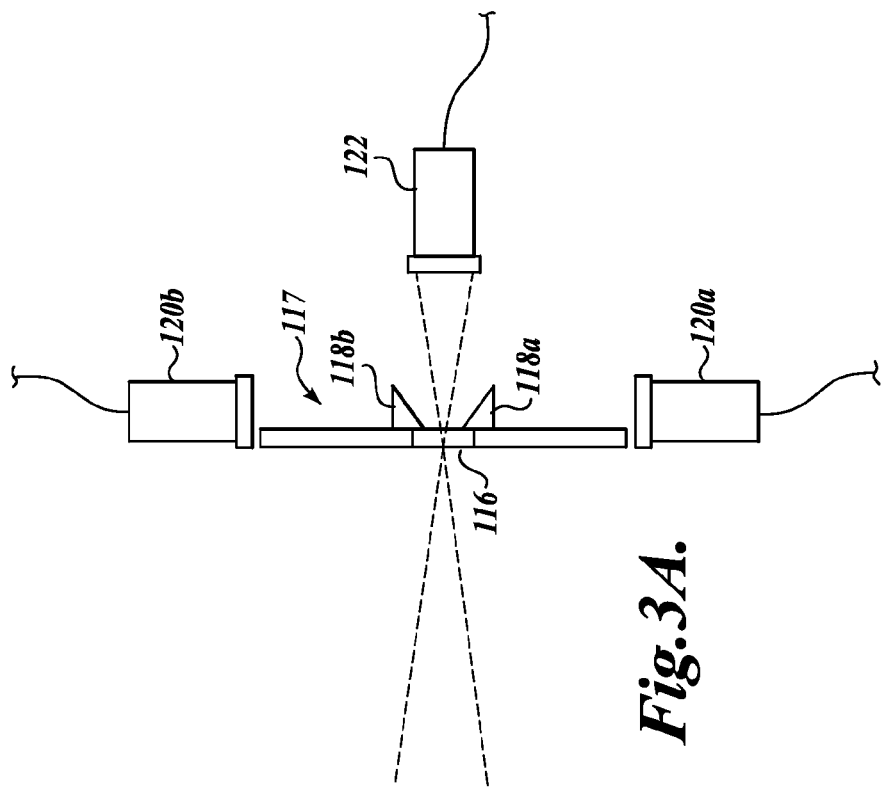
FIG. 3A is a fragmentary side schematic view indicating light focus for an in-focus particle through the optical aperture in the field stop for the cytometry system shown in FIG. 1.

To illustrate this aspect more clearly, FIG. 3A shows the field stop 117, peripheral detectors 120a, 120b and first parametric characteristic detector 122, with dashed lines indicating the light focused from a particle detected in the virtual core of the fluid stream (i.e., in focus). The light focus is directed through the center of aperture 116, and received by the first parametric characteristics detector 122 (the second parametric characteristics detector 124 and the second dichroic mirror 126 not shown, for clarity). Light for particles passing through the sensing region but not in focus (e.g., to one side, in front of, or behind the virtual core) is directed generally toward the aperture 116, but a significant portion of the light is intercepted and redirected by the peripheral prisms 118a, 118b, as shown in FIG. 3B. One or both of the peripheral detectors 120a, 120b will therefore produce a larger signal, in response to the redirected light. The signals from the peripheral detectors 120a, 120b may therefore be used to filter or gate out signals from the parametric characteristic detectors 122, 124.

Figure 4A:
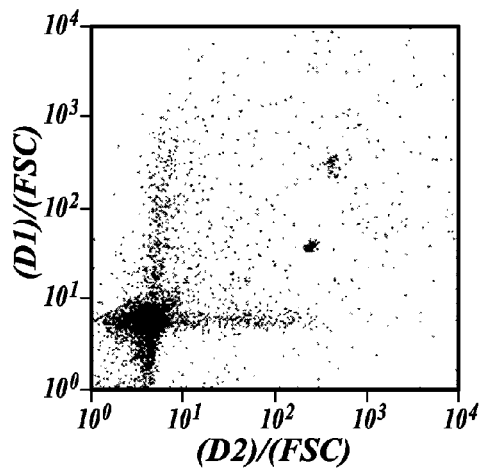
FIGS. 4A-4D are plots from detector data for an embodiment of the system shown in FIG. 1, showing differing results as the particle stream is moved from the focal portion of the sensing region.
Figure 4B:
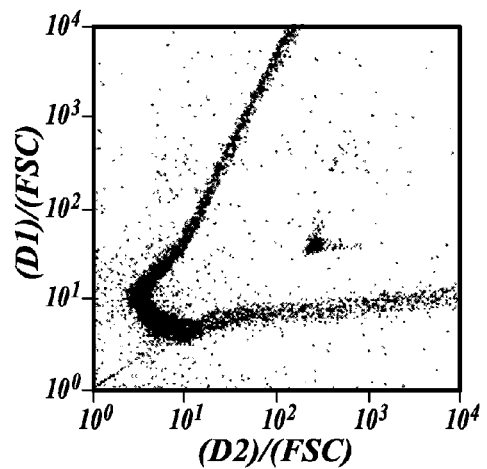
Figure 4C:
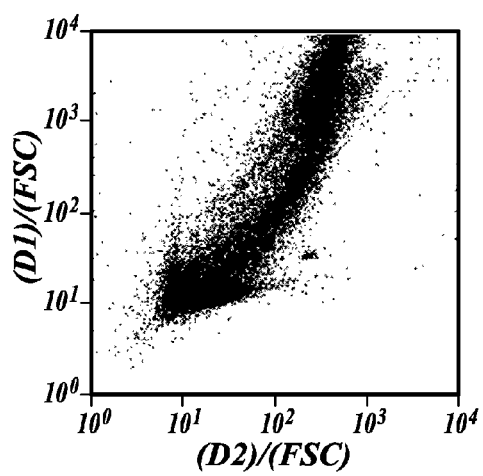
Figure 4D:
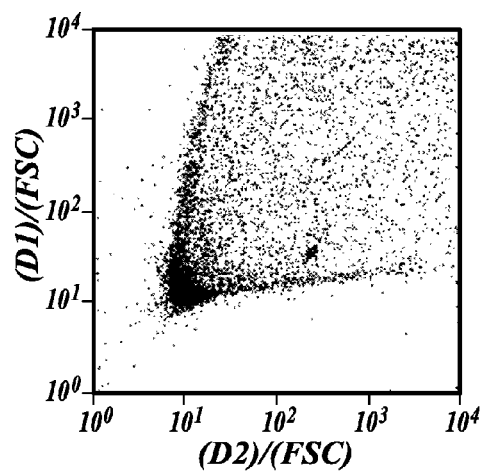

Measurement results are shown in FIGS. 4A-4D for an implementation of the system 100 using a 488 nm laser as the excitation source. Scattered and fluorescent light emission from particles in the flow cytometer fluid stream was collected using the system 100. To test the system 100, 1.0 micron polystyrene beads were added to the center of the fluid stream, and the fluid stream was moved such that the beads move in and out of the system focal area. Out-of-focus measurements were simulated by moving the stream from side to side, as well as forwards and back. FIGS. 4A-4D plot the first peripheral detector 120a signal (D1) normalized by the first parametric detector 122 signal (FSC) versus the second peripheral detector 120b signal (D2) also normalized by FSC. FIG. 4A shows the result wherein the beads are added such that the beads are in focus; FIG. 4B shows the results obtained as the fluid stream is moved back and forth by 0.001" each way from the focus; FIG. 4C shows the results obtained as the fluid stream is moved between the focus and 0.001" forward of the focus; and FIG. 4D shows the results obtained as the fluid stream is moved between focus and 0.001" rearward of focus. The data was obtained using fluorescent yellow-green 1.0 micron beads, 20× objective, and 488 nm 200 mW excitation. These plots illustrate that the normalized side detector signals (e.g., D1/FSC and D2/FSC) can be used to identify signals that are obtained from particles that are in focus in the sensing region 111 of the fluid stream.

Figure 5A:
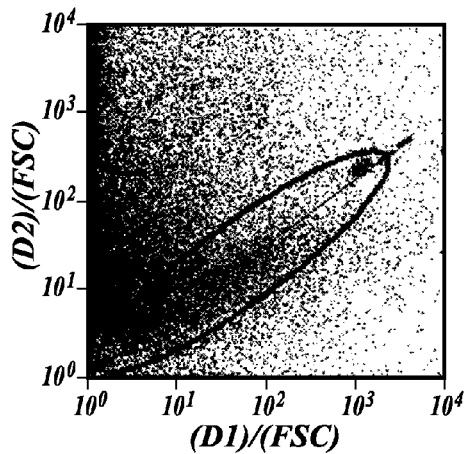
FIGS. 5A-5D are plots from detector data illustrating the effect of gating the parametric sensor data based on the identification of out-of-focus data.
Figure 5B:
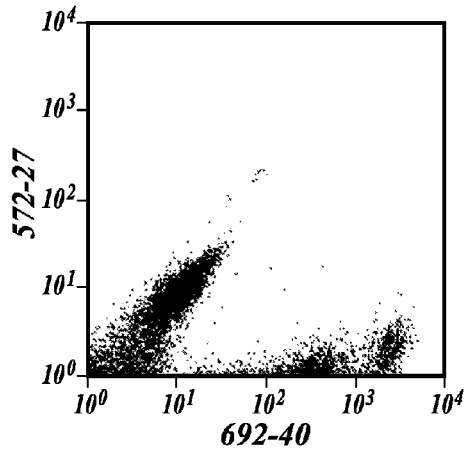
Figure 5C:
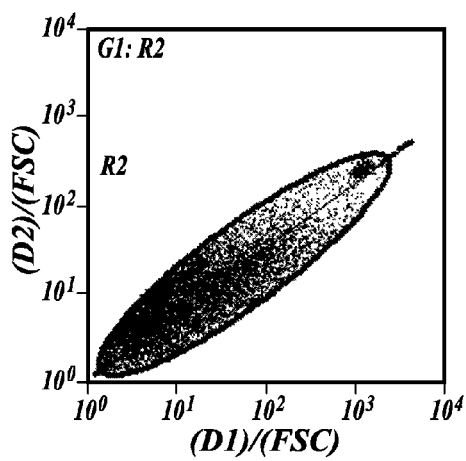
Figure 5D:
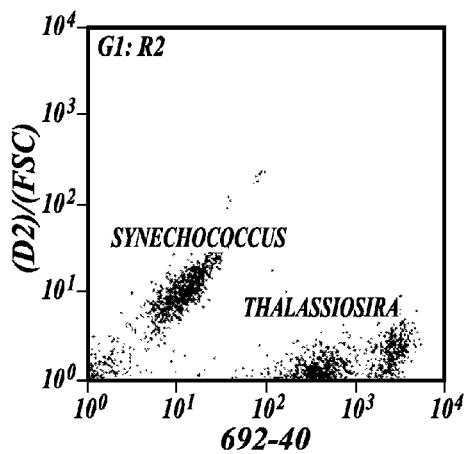

The ability of the enhanced detector 100 to measure real cell populations is depicted in FIGS. 5A-5D. A mix of marine algae was injected into a typical flow cytometer stream with the sample pressure boosted to a level where the sample flow was unsteady and not necessarily in the focal area of a 20× version of the objective 110. FIG. 5A plots the ratio of the normalized peripheral detector signals (D1/FSC v D2/FSC) as discussed above. An exemplary filter or gate profile is shown as an elongate oval oriented approximately diagonally through the data. As illustrated in FIG. 5B, only the data obtained within the filter are retained. FIG. 5C illustrates a conventional graph showing all of the data obtained, at two different frequencies (e.g., from parametric detectors 122, 124). FIG. 5D shows a similar graph, but only using the data corresponding to the individual data points corresponding to data within the filter (as shown in FIG. 5B). From the graph in FIG. 5D, persons of skill in the art would be able to determine the presence of *Synechococcus* and *Thalassiosira* in the fluid stream.

Epi-illuminescent measurement (BSC) of *Synechococcus* spp., *Thalassiosira pseudonana*, and *Thalassiosira weisfloglii* marine algae are shown; 300 mW 457 nm excitation, 20× objective. The gated region at the left is used to filter out events from particles that are not properly positioned for a measurement. Gated data showing chlorophyll versus phycoerythrin are shown at bottom right.

It will be readily understood by those persons skilled in the art that the present invention is susceptible of broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiments, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims filed and the equivalents thereof.

The functionality and reliability of the cytometry system 100 described above relies on the identification of signals from the various detectors that result from particles passing through the sensing region 111 at an out-of-focus position. Typically, such signals are excluded from the analysis. The system 100 may therefore be improved by increasing the sensitivity of the system for identifying such signals.

Figure 6:
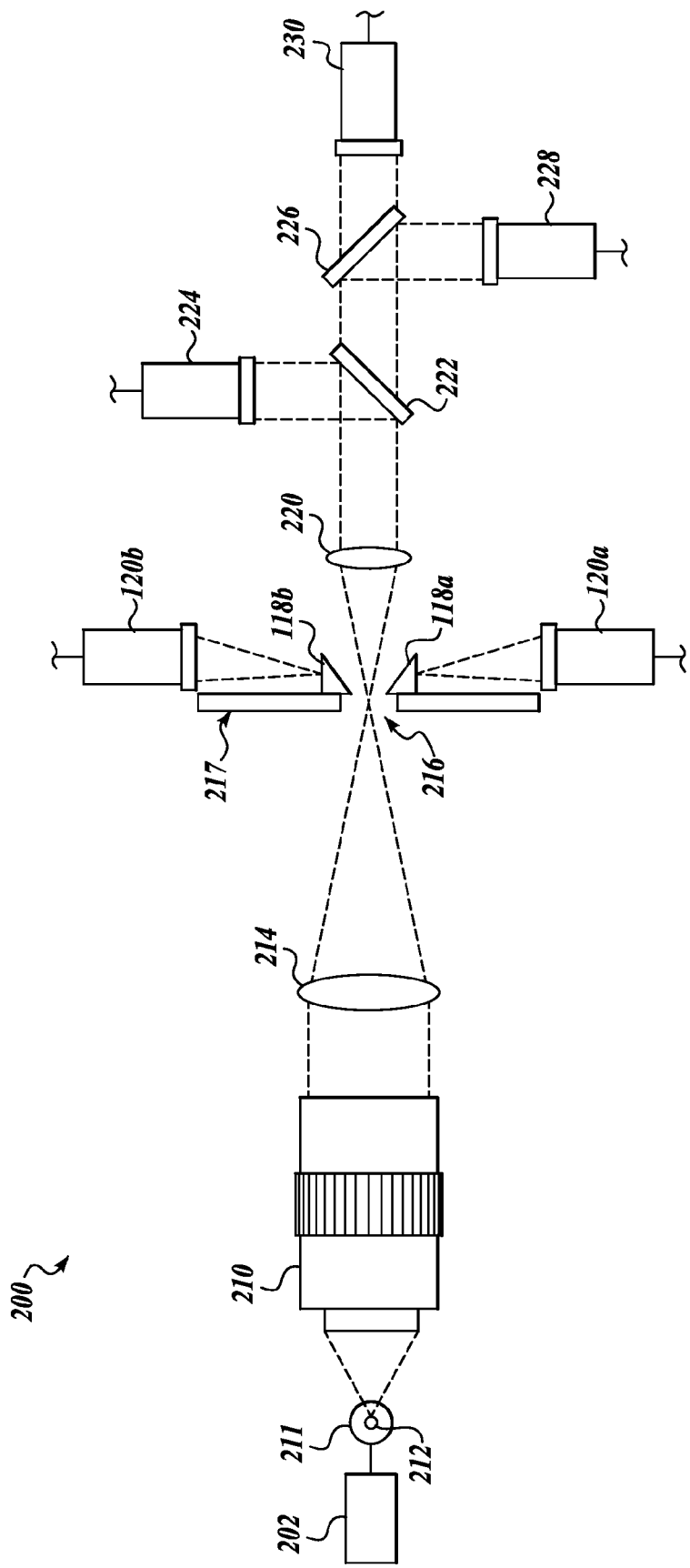
FIG. 6 is a schematic diagram of another embodiment of a cytometry system in accordance with the present invention.

Another embodiment of a cytometry system 200 in accordance with the present invention is shown in FIG. 6, wherein the laser(s) 202 illuminating the sensing region 211 are not directed through the objective 210. The system 200 is described in more detail below.

Figure 7A:
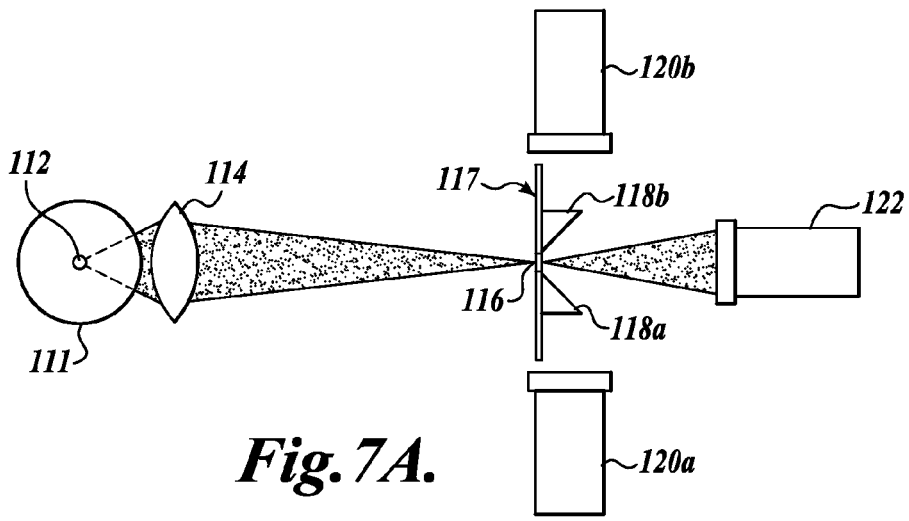
FIGS. 7A-7C illustrate schematically the operation of the detector system for in-focus and out-of-focus particle light signals.

FIG. 7A illustrates schematically light from a particle 112 within the sensing region 111 that is in a focal position. In the current embodiment the fluid stream is a vertical jet of the sample liquid, so the direction of flow of the fluid stream through the sensing region 111 is generally into the plane of the FIGURE, e.g., FIG. 7A may represent a plan view of the system. In an alternate embodiment the fluid stream may flow through a channel or passageway in an optically transparent conduit such as a quartz conduit.

Figure 7B:
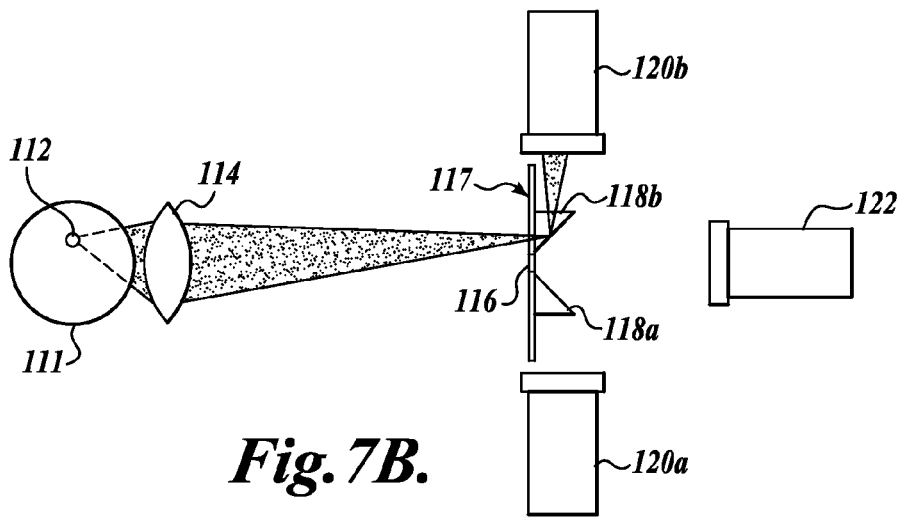
Figure 7C:
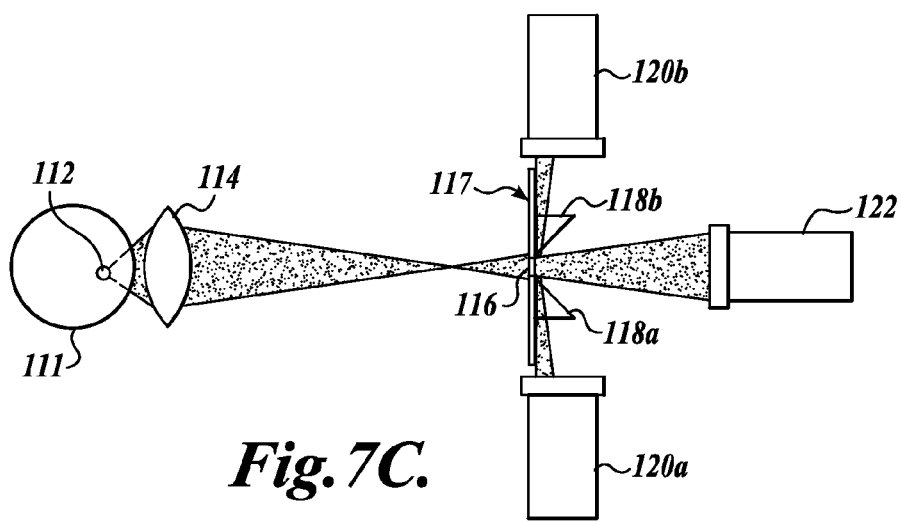

The light is focused through the optical aperture 116 in the field stop 117, and is detected by a detector such as FSC detector 122. FIG. 7B illustrates schematically similar light for a particle 112 in the sensing region that is disposed to one side of the focal area in the fluid sensing region 111 (e.g., displaced along a plane perpendicular to the optical axis of the system), such that the light image is focused slightly to one side of the optical aperture 116 in the field stop 117. At least a portion of the light is diverted by the prism 118a towards the first peripheral detector 118a. Although not shown, some of the light will typically also be detected by the FSC detector 122. FIG. 7C illustrates schematically light from a particle 112 within the sensing region 111 wherein the particle 112 is forward or behind the focal area. The image light therefore focuses before reaching the aperture 116. Therefore, the light is out of focus at the aperture 116, and a portion of the light is diverted by both prisms 118a and 118b toward the first and second peripheral detectors 120a and 120b.

Figure 8A:
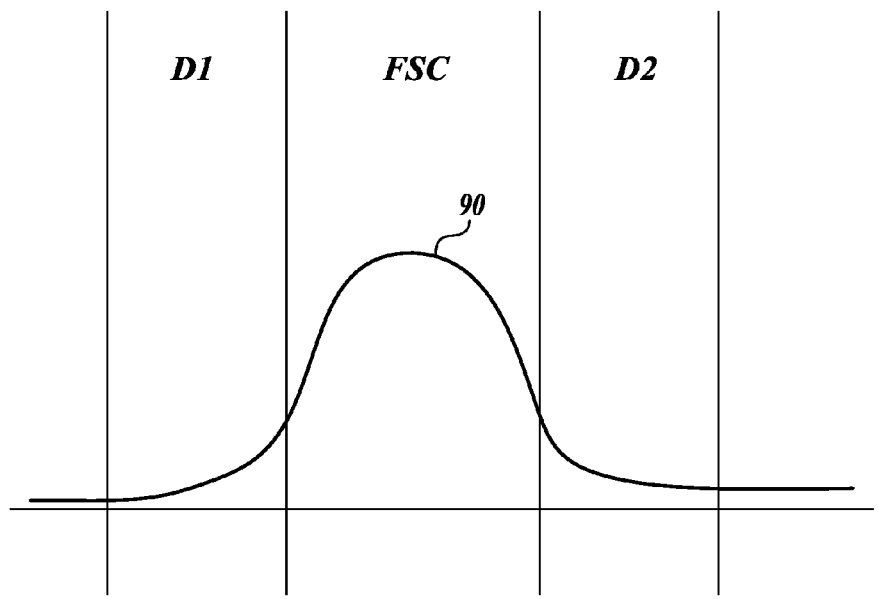
FIGS. 8A-8B illustrate the motivation for using a field stop with an optical aperture having relatively large end portions and a relatively small center portion.

It will be appreciated that the light arriving at the proximal side of the field stop 117a near the aperture 116 will have an intensity distribution that is in general greater near the center, and drops off rapidly away from the peak, such as (qualitatively) a two-dimensional Gaussian shape. As illustrated in FIG. 8A, an exemplary idealized light profile 90 for an out-of-focus particle that is in front of or behind the focal point will substantially pass through the aperture 116 to the FSC detector 122, and only the light from the tail portion of the profile 90 is diverted by the prisms 118a, 118b to the peripheral detectors 120a, 120b. Therefore, the detector system may not have the desired sensitivity to detect signals from out-of-focus particles.

Figure 9A:
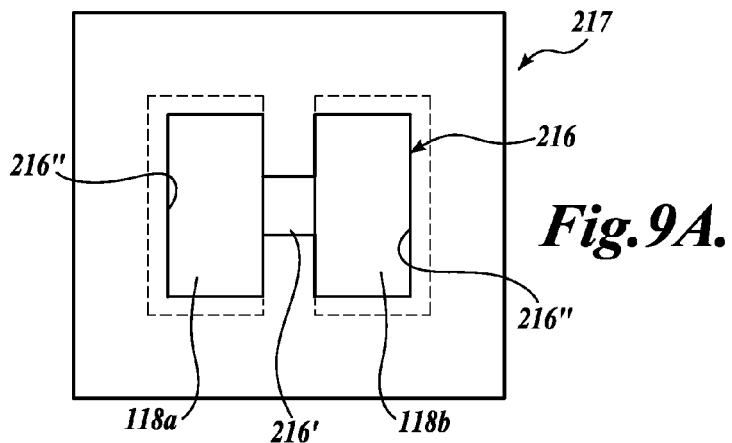
FIGS. 9A-9C show three embodiments of field stops for the in accordance with the present invention.

FIG. 9A shows an alternative field stop 217 wherein the optical aperture 216 is a shaped aperture having a relatively small center portion 216' and oppositely disposed, relatively large end portions 216". In this embodiment the shaped aperture 216 is generally H-shaped. The first and second light deflectors or prisms 118a, 118b are each disposed over the relatively large end portions 216" of the aperture 216.

Figure 8B:
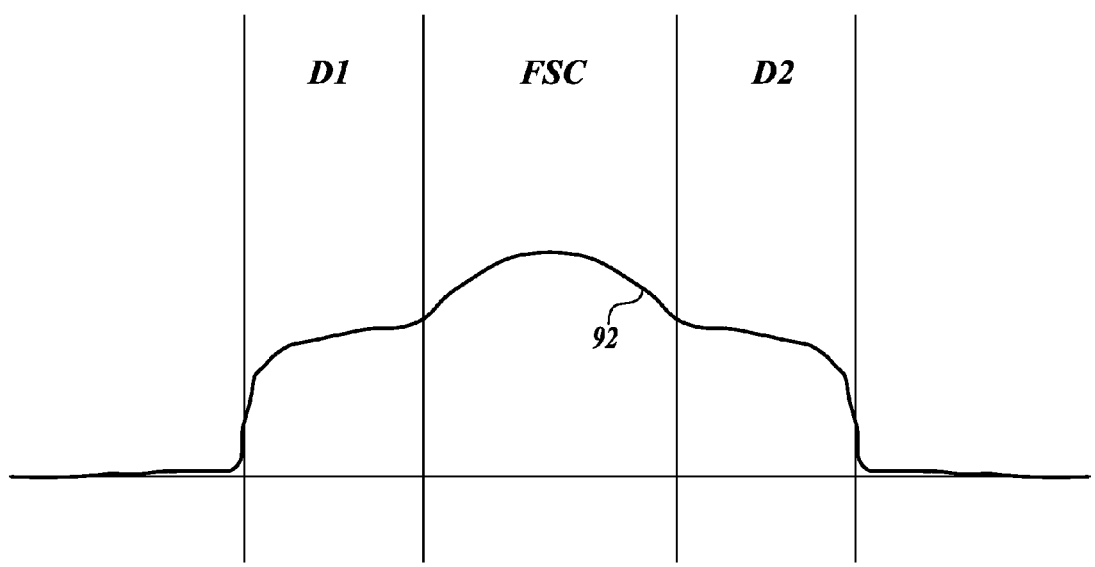

The H-shaped aperture 216 increases the amount of light arriving at the field stop 217 to pass through the aperture 216, and in particular to increase the light deflected to the peripheral detectors 120a, 120b for out-of-focus particles. The larger end portions 216" of the aperture 216 improve the ability of the system to detect and identify out-of-focus particles, allowing a greater portion of the tail portion of the light reaching the field stop 217 to reach the peripheral detectors 120a, 120b, producing an effective light profile qualitatively as indicated by curve 92 in FIG. 8B.

Figure 9B:
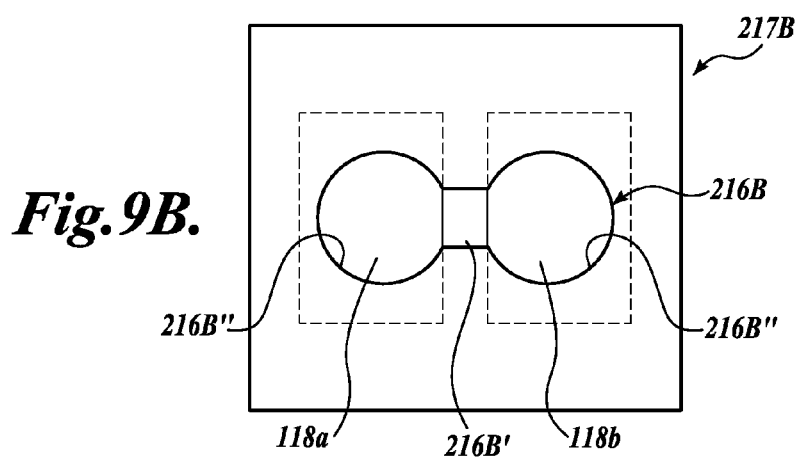
Figure 9C:
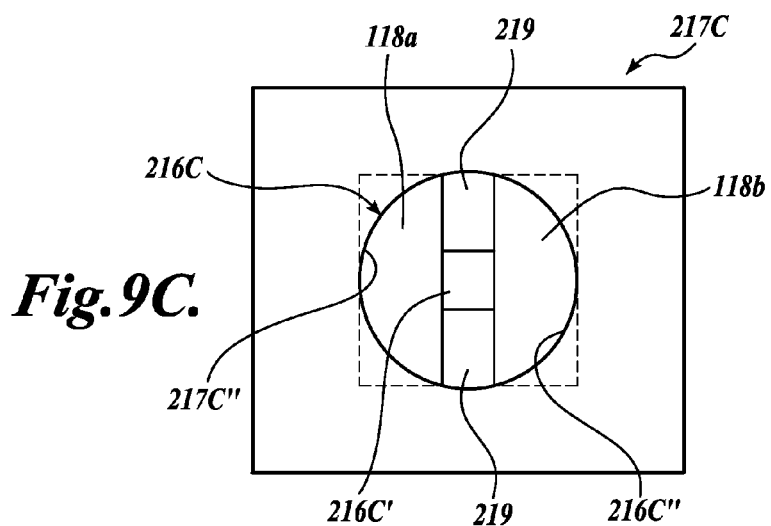

Although the H-shaped aperture 216 is currently preferred, it will be appreciated that the shaped aperture may be formed in alternative shapes. For example, FIG. 9B illustrates an exemplary field stop 217B wherein the light aperture 216B is a shaped aperture having a relatively small center portion 216B' and oppositely disposed, relatively large end portions 216B". In this embodiment, the relatively large end portions 216B" are substantially circular. Similarly, FIG. 9C illustrates an exemplary field stop 217C wherein the light aperture 216C is a shaped aperture having a relatively small center portion 216C' and oppositely disposed, relatively large end portions 216C". In this embodiment, the aperture 216C is produced by forming a large circular optical aperture, and attaching oppositely disposed radial light blocking elements 219 that extend from the edge part way towards the center of the large circular aperture. Other obvious variations of the shaped aperture will be apparent to persons of skill in the art.

Referring again to FIG. 6 shows a cytometry system 200 similar to the system 100. In this system 200 one or more lasers 202 are directed through a sensing region 211 through which flows a fluid stream containing particles 212 of interest. The microscope objective 210 receives light from the particles (e.g., scatter and/or fluorescence) which is focused by a lens 214 through the H-shaped aperture 216 in the field stop 217 (see, FIG. 9A). In FIG. 6, the light is indicated with dashed lines for a particle 212 located in the focal area of the sensing region 211. In general, the light may include one or both of light scattered by the particles and light fluorescent from the particles. As illustrated in FIGS. 7A-7C, light for particles not in the focal area will have a larger portion deflected by one or both of the prisms 118a, 118b to the peripheral detectors 120a, 120b.

In this embodiment light transmitted through the optical aperture 216 (and not deflected) is directed through lens 220 to a beam splitter such as a 4% transmission mirror 222 that reflects a portion of the light to a forward scan detector 224 and transmits a portion of the light which encounters a dichroic mirror 226 that selectively filters the light according to wavelength. For example, the dichroic mirror 226 reflects a portion of the light to a first phosphorescence light detector 228, and transmits a portion of the light which encounters a second (e.g., PE-Cy5) phosphorescence light detector 230. For simplicity, the controller 130 (FIG. 1), and the signal communications therewith are not shown. However, as discussed above, the system 200 uses the detector signals from the first and second peripheral detectors 120a, 120b to identify light responses for out-of-focus particles in the sensing region 211, which may then be excluded from the analysis.

While illustrative embodiments have been illustrated and described, it will be appreciated that various changes can be made therein without departing from the spirit and scope of the invention.

The embodiments of the invention in which an exclusive property or privilege is claimed are defined as follows:

1. A cytometry system for analyzing a fluid stream having a plurality of suspended particles in the fluid stream, the system comprising:

a light source for directing light through a sensing region in the fluid stream;

an objective positioned to receive light from the sensing region of the fluid stream, wherein the received light includes information about suspended particles that pass through the sensing region;

a lens positioned to locus the light received by the objective;

a field stop having a shaped optical aperture comprising a relatively small center portion, and relatively large first and second end portions wherein the lens is positioned to focus the received light onto the shaped aperture;

a light detector system comprising a scatter light detector operable to receive light that is focused by the lens on the relatively small center portion of the aperture, and first and second peripheral light detectors;

a first light deflector positioned over the relatively large first end portion of the shaped aperture and operable to deflect light from the lens that is incident on the first light deflector towards the first peripheral light detector, and a second light deflector positioned over the relatively large second end portion of the shaped aperture and operable to deflect light from the lens that is incident on the second light deflector towards the second peripheral light detector, wherein each of the first and second light deflectors overlie a portion of the shaped aperture that is larger than the relatively small center portion; and a controller operably connected to receive signals from the scatter light detector and from the first and second peripheral light detectors.

2. The cytometry system of claim 1, wherein the shaped aperture is H-shaped.

3. The cytometry system of claim 1, wherein the shaped aperture is defined by a large optical aperture and a pair of light blocking elements disposed radially from opposite sides of the large aperture.

4. The cytometry system of claim 1, wherein the scatter light detector comprises a photomultiplier tube.

5. The cytometry system of claim 1, wherein the first and second light deflectors comprise prisms.

6. The cytometry system of claim 1 wherein the controller selects signals from the scatter light detector for use in analysis based on the corresponding signals received from the first and second peripheral light detectors.

7. The cytometry system of claim 6, wherein the scatter light detector signals received by the controller are disregarded if the ratio of the corresponding signal from at least one of the first and second peripheral light detectors to the scatter light detector signal exceeds a predetermined value.

8. The cytometry system of claim 1, wherein the light source is a first laser.

9. The cytometry system of claim 8, further comprising a second laser for directing light through a sensing region in the fluid stream, wherein the second laser produces light having a different frequency than the first laser.

10. The cytometry system of claim 1, wherein the fluid stream comprises a water stream and the particles comprise cells.

11. A method of cytometry for detecting microscopic particles in a fluid stream comprising:
flowing a sheathless fluid stream containing a plurality of the microscopic particles through a sensing region;
transmitting light from a light source through the fluid stream at the sensing region such that at least some of the microscopic particles in the fluid stream scatter the transmitted light, and wherein only a portion of the microscopic particles pass through a focal region of interest in the fluid stream;
providing a field stop having a shaped optical aperture in alignment with the transmitted light, wherein the shaped aperture includes a relatively small center portion and relatively large first and second end portions, the field stop further comprising a first light deflector disposed over the first end portion of the shaped aperture and a second light deflector disposed over the second end portion of the shaped aperture such that the first and second right deflectors each overlie a portion of the shaped aperture that is larger than the relatively small center portion;
focusing the light scattered by the microscopic particles passing through the sensing region such that light scattered by microscopic particles passing through a local core of the stream is focused on the center portion of the shaped aperture;
detecting with a scatter light detector light passing through the center portion of the shaped aperture to produce a scatter light signal;
detecting with first and second peripheral light detectors light intercepted by the first and second light deflectors to produce deflected light signals that correspond to the detected scatter light signal;
using the deflected light signals, identifying scatter light signals that correspond to microScopic particles passing through the focal core of the stream.

12. The method of claim 11, wherein the shaped optical aperture is H-shaped.

13. The method of claim 11, wherein the shaped optical aperture is defined by a large optical aperture and a pair of light blocking elements disposed radially from opposite sides of the large aperture.

14. The method of claim 11, wherein the scatter light detector comprises a photomultiplier tube.

15. The method of claim 11, wherein the first and second light deflectors comprise prisms.

16. The method of claim 11 further comprising providing a controller that is operably connected to receive the scatter light signal and the deflected light signals, wherein the controller selects scatter light signals for use in additional analysis based on the corresponding deflected light signals.

17. The method of claim 16, wherein the scatter light signal is disregarded if the ratio of either of the deflected light signals to the scatter light signal exceeds a predetermined value.

18. The method of claim 11, wherein the sheathless fluid stream comprises water stream and the microscopic particles comprise cells.

* * * * *

UNITED STATES PATENT AND TRADEMARK OFFICE
CERTIFICATE OF CORRECTION

| | |
|---|---|
| PATENT NO. | : 8,467,054 B2 |
| APPLICATION NO. | : 13/145772 |
| DATED | : June 18, 2013 |
| INVENTOR(S) | : J. E. Swalwell |

It is certified that error appears in the above-identified patent and that said Letters Patent is hereby corrected as shown below:

In the Claims:

| COLUMN | LINE | ERROR |
|---|---|---|
| 9 (Claim 1, | 7 line 10) | "locus" should read --focus-- |
| 9 (Claim 1, | 11 line 14) | after "portions" insert --,-- |
| 10 (Claim 11, | 19 line 19) | "right" should read --light-- |
| 10 (Claim 11, | 24 line 24) | "local" should read --focal-- |
| 10 (Claim 11, | 35 line 35) | "microScopic" should read --microscopic-- |

Signed and Sealed this
Twenty-ninth Day of April, 2014

Michelle K. Lee
*Deputy Director of the United States Patent and Trademark Office*